United States Patent [19]

Gilbert

[11] 4,270,012

[45] May 26, 1981

[54] PREPARATION OF HNS FROM HNBB USING OXYGEN

[75] Inventor: Everett E. Gilbert, Morristown, N.J.

[73] Assignee: The United States of America as represented by the Secretary of the Army, Washington, D.C.

[21] Appl. No.: 112,585

[22] Filed: Jan. 16, 1980

[51] Int. Cl.$^3$ ............................................. C07C 79/10
[52] U.S. Cl. ................................................... 568/931
[58] Field of Search ...................................... 568/931

[56] References Cited

U.S. PATENT DOCUMENTS

| 3,505,413 | 4/1970 | Shipp | 568/931 |
| 3,716,590 | 2/1973 | Caraculacu et al. | 568/931 |
| 3,895,055 | 7/1975 | Itatani | 568/931 |
| 4,085,152 | 4/1978 | Salter et al. | 568/931 |

FOREIGN PATENT DOCUMENTS 2256144  7/1975  France ..................................... 568/931

*Primary Examiner*—Leland A. Sebastian
*Attorney, Agent, or Firm*—Nathan Edelberg; Robert P. Gibson; A. Victor Erkkila

[57] ABSTRACT

A process for preparing 2,2',4,4',6,6'-hexanitrostilbene in high yields by reacting 2,2',4,4',6,6'-hexanitrobibenzyl in a suitable solvent with an oxygen-containing gas in the presence of a catalyst. The catalyst is selected from the group consisting of copper ammino and cobalt ammino compounds, copper and cobalt acetates, copper and cobalt halides, copper sulfate, and ammonium and alkali metal bases.

10 Claims, No Drawings

PREPARATION OF HNS FROM HNBB USING OXYGEN

DEDICATORY CLAUSE

The invention described herein may be manufactured, used, and licensed by or for the Government for governmental purposes without the payment to me of any royalty thereon.

BACKGROUND OF THE INVENTION

The present invention relates to a process for preparing 2,2',4,4',6,6'-hexanitrostilbene (HNS) through oxidation of 2,2',4,4',6,6'-hexanitrobibenzyl (HNBB) with oxygen containing gas in the presence of a catalyst.

2,2',4,4',6,6'-Hexanitrostilbene (HNS) is a thermally stable explosive. HNS has also been used as a nucleating agent for promoting a desired mode of crystallization of 2,4,6-trinitrotoluene (TNT) in melt-cast TNT explosives.

HNS has been prepared in rather low yields by oxidation of TNT. Thus, Shipp, U.S. Pat. No. 3,505,413, NOLTR (U.S. Naval Ordnance Laboratory Technical Report) 64-34 (1964), and Shipp and Kaplan, Journal of Organic Chemistry, 31,857 (1966), disclose a process which comprises reacting TNT with sodium hypochlorite in a solvent mixture consisting of two parts tetrahydrofuran (THF) and one part methanol by volume to produce crude HNS in yields of 40-45% of theory. The crude HNS, which contains substantial amounts of co-precipitated impurities, is purified by extraction with hot acetone. Shipp and Kaplan disclose that TNT can be converted to HNBB or HNS with sodium hypochlorite under various conditions, with a yield of 79% HNBB from TNT. No procedure for preparing HNS from HNBB is disclosed.

The British Patent application No. 76/2501 to Salter et al, Jan. 22, 1976, discloses a process wherein TNT is reacted in THF-methanol solution with sodium hypochlorite at approximately 10°-20° C., with subsequent addition of an aqueous solution of an organic amine, preferably trimethylamine. This process gives yields of approximately 50% of theory.

Kompolthy et al, Hungarian Patent T/9639 VE-719 (C06f9/04) discloses a process for air oxidation of TNT to produce HNS in two steps as follows:

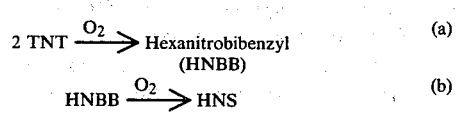

They disclose yields of 82% HNBB and 76-91% HNS from HNBB by employing dimethylformamide or dimethylsulfoxide as solvents in a reaction mixture comprising methanol, potassium hydroxide, copper sulfate and pyridine. Efforts to repeat this procedure have only been successful in yielding 25-40% HNS.

Thus, there has been a need for a process for production of HNS in high reproducible yields.

In my copending U.S. Patent application, Ser. No. 069,216, filed Aug. 23, 1979, I have disclosed a process of producing good yields of HNS by reacting HNBB with copper sulfate in a reaction medium consisting essentially of hexamethylphosphoric triamide (HMPT) solvent. The process further discloses that the amount of copper sulfate used can be reduced much below stoichiometric amounts when a stream of an oxygen-containing gas, e.g., air is introduced into the reaction mixture. Substantially lower yields were obtained when the solvents N,N-dimethylformamide, N-methylpyrrolidinone, dimethylsulfoxide, pyridine and tetramethylurea were used in place of HMPT. Similarly, other copper and cobalt salts in hexamethylphosphoramide gave considerably lower yield of HNS than copper (II) sulfate, with copper acetate being only moderately effective (58% yield) while copper bromide, copper chloride, cobalt chloride, cobalt acetate and a cobalt ethylene-diamine-2,4-pentanedione complex gave poor yields.

My other copending U.S. Patent application, Ser. No. 020,881, filed Mar. 15, 1979, discloses and claims preparation of HNS by reacting HNBB with a copper ammino compound, e.g., copper tetraamminosulfate in a solvent including hexamethylphosphoramide (HMPT).

A process for converting HNBB to HNS through reaction of HNBB with a halogenating agent in the presence of a base and a suitable solvent is disclosed in copending U.S. Patent application, Ser. No. 020,889 by Everett E. Gilbert, filed Mar. 15, 1979. The halogenating agents include chlorine, bromine, iodine, N-halogen derivatives, e.g., N-chlorosuccinimide, N-bromosuccinimide and N-bromoacetamide, and hypohalites. The base used can be organic, e.g., tertiary amines such as pyridine and triethylamine or inorganic, e.g., sodium hydroxide, ammonium hydroxide, magnesium oxide, sodium carbonate and sodium bicarbonate. Acceptable yields of HNS were obtained with a pyridine base and the preferred bromine or N-bromosuccinimide halogenating agents.

Though prior methods have been successful in producing acceptable yields of HNS, there remains a need for a simplified process for producing HNS in high reproducible yields.

BRIEF SUMMARY OF THE INVENTION

A process for preparing 2,2',4,4',6,6'-hexanitrostilbene in high yields by reacting 2,2',4,4',6,6'-hexanitrobibenzyl in a suitable solvent with an oxygen-containing gas in the presence of a catalyst. The catalyst is selected from the group consisting of copper ammino and cobalt ammino compounds, copper and cobalt acetates, copper and cobalt halides, copper sulfate, and ammonium and alkali metal bases.

It is an object of the present invention to provide a process for preparing 2,2',4,4',6,6'-hexanitrostilbene (HNS) in high yields through the oxidation of 2,2',4,4',6,6'-hexanitrobibenzyl (HNBB).

It is a further object of this invention to provide a process for the preparation of HNS through oxidation of HNBB with an oxygen containing gas without requiring the use of methanol, potassium hydroxide, pyridine and other solvents essential in the Kompolthy et al process discussed above.

It is a still further object of this invention to provide a process for preparing 2,2',4,4',6,6'-hexanitrostilbene through oxidation of HNBB with oxygen-containing gas in increased yields through addition of small amounts of a catalyst.

These and other objects of the invention will be apparent from the detailed description of the invention.

DETAILED DESCRIPTION OF THE INVENTION

In accordance with the process of the present invention, 2,2',4,4',6,6'-hexanitrostilbene (HNS) can be produced in good yields by oxidizing 2,2',4,4',6,6'-hexanitrobibenzyl (HNBB) in an appropriate solvent with oxygen as an oxidant in the following reaction:

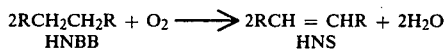

$$2RCH_2CH_2R + O_2 \longrightarrow 2RCH=CHR + 2H_2O$$
$$\text{HNBB} \qquad\qquad\qquad \text{HNS}$$

wherein R=2,4,6-trinitrophenyl.

The oxygen can be provided as pure oxygen gas or in an oxygen containing gas such as air.

The yields obtained by oxidation of HNBB with oxygen can be increased by the addition of small amounts of various promoters or catalysts. In particular, the catalysts which have been found to give substantially increased yields of HNS include ammino compounds selected from the group consisting of copper and cobalt ammino compounds, copper sulfate and bases selected from the group consisting of ammonium and alkali metal bases. Other catalysts, such as copper acetate, were moderately effective in increasing yields of HNS. Copper bromide and cobalt compounds including cobalt chloride, cobalt acetate and cobalt-ethylene diamine-acetylacetone complex were poorly effective in the process of this invention.

The liquid solvents used in this invention are those in which the reactants are readily dissolved or suspended and which do not interfere with the reaction. Typical solvents which are suitable and give similar results are, N,N-dimethylformamide, N-methylpyrrolidinone and hexamethylphosphoramide. The preferred solvent for use in this process is dimethylformamide, since it is readily available, least costly, and gives the best consistently high yields of HNS, both with or without the novel oxidation catalysts of this invention. The use of N,N-dimethylacetamide and to a lesser extent, dimethylsulfoxide give lower yields of HNS, particularly without the use of a catalyst, and are therefore less preferred. Solvents which appear to be unsatisfactory, since no yields were obtained, even with oxidation catalysts, include, N,N-dimethylaniline, sulfolane and tetrahydrofuran.

The present process can be carried out at temperatures ranging from about room temperature (20° C.) to about 100° C., although it is not limited thereto. The reaction times and temperatures are important to the extent that each reaction mixture with different and various amounts of starting material, solvent and catalyst requires different reaction times and temperatures to proceed to completion for optimum yield of HNS product. Thus, for example, when 1.2 g HNBB in 15 ml N,N-dimethylformamide (DMF) are treated with air (30 ml/min.) and reacted for 16 and 40 hours at room temperature, the respective yields of HNS are 63% and 75%. When 0.05 g copper tetramminosulfate catalyst is added, the yield went up to 88% after 16 hours. Therefore, each reaction mixture would be reacted for a time and at a temperature which would result in optimum yield.

The relative amounts of the catalysts used in the process are not critical, unlike prior art processes (such as that disclosed in U.S. Patent application, Ser. No. 020,881.) The catalysts are effective in very small amounts, i.e., on the order of 0.05 g-0.1 g catalyst per 1.2 g HNBB, but larger amounts can obviously be used without affecting yield. Small amounts of catalyst are obviously preferred for economic reasons.

The following examples illustrate the process of this invention and are not to be interpreted in a limiting sense:

EXAMPLE 1-17 OXIDATION OF HNBB TO HNS WITH OXYGEN CONTAINING GAS (WITHOUT CATALYST/PROMOTER)

HNBB (1.2 g) was dissolved . . . the yield was 0.75 g (63%).

The procedure of example 1 was repeated in examples 2-17 with appropriate changes in solvent, oxygen containing gas and reaction time and temperature as indicated in the following table of summarized results:

USE OF PURE SOLVENTS

| Example No. | Solvent | Gas | Temp °C. | Reaction Time (hrs) | % Yield HNS |
|---|---|---|---|---|---|
| 1 | N,N-Dimethylformamide | Air | Room | 16 | 63 |
| 2 | N,N-Dimethylformamide | Air | Room | 6 | 0 |
| 3 | N,N-Dimethylformamide | Air | Room | 40 | 75 |
| 4 | N,N-Dimethylformamide | O$_2$ | 70 | 3 | 21 |
| 5 | Pyridine | Air | Room | 16 | 17 |
| 6 | Pyridine | O$_2$ | 70 | 3 | 13 |
| 7 | N-Methylpyrrolidinone | Air | Room | 16 | 13 |
| 8 | N-Methylpyrrolidinone | O$_2$ | 70 | 3 | 42 |
| 9 | Hexamethylphosphoramide | Air | Room | 16 | 33 |
| 10 | Hexamethylphosphoramide | O$_2$ | 70 | 4 | 0 |
| 11 | Dimethyl sulfoxide | Air | 80 | 2 | 5 |
| 12 | Dimethyl sulfoxide | Air | Room | 16 | 0 |
| 13 | Dimethyl sulfoxide | O$_2$ | 70 | 3 | 25 |
| 14 | Sulfolane | Air | Room | 65 | 0 |
| 15 | N,N-Dimethylacetamide | Air | Room | 65 | 0 |
| 16 | Tetrahydrofuran | Air | Room | 18 | 0 |
| 17 | N,N-Dimethylaniline | Air | Room | 16 | 0 |

Applicant has found the use of small amounts of catalyst or promoter materials facilitate the use of oxygen for the oxidation of HNBB to HNS. In applicant's copending U.S. Patent application, Ser. No. 020,881, filed Mar. 15, 1979, it is shown that HNBB can be converted to HNS by treatment with copper ammino compounds, with copper tetrammino sulfate giving the best results. Contrary to the teaching in this disclosure that good yields are critically dependent upon amount of copper tetrammino sulfate, with stoichiometric quantities being necessary for optimum yields, applicant has unexpectedly found that even greater yields of HNS can be obtained with very small amounts of copper tetrammino sulfate. The effectiveness of catalytic amounts of copper and cobalt ammino compounds in facilitating oxygen oxidation of HNBB to HNS can be seen in the following tables summarizing the results of Examples 18-25:

EXAMPLES 18-25

The procedure of Example 1 was followed with all runs using 1.2 g HNBB, 15 ml solvent, and 0.05 g copper tetrammino sulfate for 16 hours at room temperature with air, except as indicated.

| PROMOTION OF OXIDATION WITH AMMINO COMPOUNDS | | | |
|---|---|---|---|
| Example No. | Solvent | % Yield HNS | Yield Without Ammino (Example from Table 1) |
| 18 | N,N-Dimethylformamide | 88 | 63 (1) |
| 19 | N,N-Dimethylformamide | 92 (1) | 63 (1) |
| 20 | N,N-Dimethylformamide | 84 (2) | 63 (1) |
| 21 | N-Methylpyrrolidinone | 75 | 13 (7) |
| 22 | N,N-Dimethylacetamide | 84 | 0 (15) |
| 23 | Dimethylsulfoxide | 79 | 0 (12) |
| 24 | Pyridine | 79 (3) | 17 (5) |
| 25 | Hexamethylphosphoramide | 71 | 33 (9) |

(1) Added 0.1g copper compound.
(2) Used 0.05g cobalt nitrate tetrammino carbonate complex [Co(NH$_3$)$_4$CO$_3$]NO$_3$ . 0.5 H$_2$O.
(3) Used 30 ml solvent.

In my copending U.S. Patent application, Ser. No. 020,881, filed Mar. 15, 1979, I have disclosed the use of copper sulfate in converting HNBB to HNS with copper sulfate being unequally effective with hexamethylphosphoramide and considerably less so with other solvents. The following tests show that copper sulfate is also effective as a promoter/catalyst and is submitted to permit comparison with other systems. The results also show that copper acetate is effective as a promoter, while copper bromide and three cobalt compounds tested were only partially effective in achieving increased yields of NHS.

EXAMPLES 26-36

All runs were made using 1.2 g HNBB, 0.1 g anhydrous copper sulfate, and oxygen for 3 hours at 70° C., except as indicated:

| PROMOTION WITH COPPER SULFATE | | | |
|---|---|---|---|
| Example No. | Solvent | % Yield HNS | Yield Without CuSO$_4$ |
| 26 | Hexamethylphosphoramide | 83 | 0 (10) |
| 27 | Hexamethylphosphoramide | 83 (1) | 0 (10) |
| 28 | Hexamethylphosphoramide | 75 (2) | — |
| 29 | Hexamethylphosphoramide | 58 (3) | 0 (10) |
| 30 | Hexamethylphosphoramide | 33 (4) | 0 (10) |
| 31 | Hexamethylphosphoramide | 33 (5) | 0 (10) |
| 32 | Hexamethylphosphoramide | 33 (6) | 0 (10) |
| 33 | Hexamethylphosphoramide | 33 (7) | 0 (10) |
| 34 | N,N-Dimethylformamide | 54 | 21 (4) |
| 35 | Dimethyl sulfoxide | 54 | 25 (13) |
| 36 | Pyridine | 58 | 13 (6) |

(1) Used equivalent CuSO$_4$ . 5H$_2$O in this run.
(2) Used air instead of oxygen in this run.
(3) Used CuAc$_2$ . H$_2$O(0.13g, equivalent to 0.1g CuSO$_4$).
(4) Used CuBr$_2$ (0.14g, equivalent to 0.1g CuSO$_4$).
(5) Used CoCl$_2$ . 6H$_2$O (0.15g, equivalent to 0.1g CuSO$_4$).
(6) Used CoAc$_2$ . 4H$_2$O (0.16g, equivalent to 0.1g CuSO$_4$).
(7) Used cobalt-ethylene diamine-acetylacetone complex (0.3g).

In addition to the above disclosed copper and cobalt compound catalysts, it has also been found that the addition of small amounts of basic materials, selected from the group consisting of ammonium and alkali metal bases, will promote oxidation of HNBB with oxygen containing gas, as shown in the following examples:

EXAMPLES 37-52

All runs were made using air for 6 hours at room temperature with 1.2 g HNBB and 15 ml DMF solvent, with the amount of catalyst indicated:

| PROMOTION WITH BASIC COMPOUNDS | | | |
|---|---|---|---|
| Example No. | Catalyst | % Yield HNS | Amount of Catalyst (g) |
| 37 | NH$_4$OH | 67 | 0.05 g |
| 38 | NH$_4$OH | 75 | 0.1 g |
| 39 | NaNO$_2$ | 42 | 0.2 g |
| 40 | KNO$_2$ | 54 | 0.05 g |
| 41 | MgO | 42 | 0.12 g |
| 42 | MgCO$_3$(basic) | 29 | 0.05 g |
| 43 | MgCO$_3$(pure) | 13 | 0.05 g |
| 44 | | | |
| 45 | NaCN | 29 | 0.05 g |
| 46 | Na Acetate | 33 | 0.1 g |
| 47 | NH$_4$Acetate | 42 | 0.1 g |
| 48 | NH$_4$HCO$_3$ | 50 | 0.05 g |
| 49 | Na$_3$PO$_4$ . 12H$_2$O | 58 | 0.05 g |
| 50 | ZnO | 50 | 0.05 g |
| 51 | NaHCO$_3$ | 50 | 0.05 g |
| 52 | KHCO$_3$ | 58 | 0.05 g |

The present invention does not include the use of copper sulfate with hexamethylphosphoramide, hexamethylphosphoric triamide (HMPT), as disclosed in U.S. Patent application, Ser. No. 020,881, filed Mar. 15, 1979.

The foregoing disclosure is merely illustrative of the principles of this invention and is not to be interpreted in a limiting sense. Applicant does not desire to be limited to the exact details of construction shown since obvious modifications will occur to one skilled in the art.

I claim:

1. A method for preparing 2,2',4,4',6,6'-hexanitrostilbene comprising the step of treating 2,2',4,4',6,6'-hexanitrobibenzyl in an appropriate solvent with an oxygen containing gas.

2. The method of claim 1 wherein the solvent is selected from the group consisting of N,N-dimethylformamide, pyridine, N-methylpyrrolidinone, hexamethylphosphoramide, N,N-dimethylacetamide, and dimethylsulfoxide.

3. The method of claim 2 wherein the solvent is N,N-dimethylformamide.

4. The method of claim 2 further including the step of using a relatively small amount of a catalyst selected from the group consisting of copper ammino and cobalt ammino compounds, copper and cobalt acetate, copper and cobalt halides, and ammonium and alkali metal bases.

5. The method of claim 4 where the bases are selected from the group consisting of ammonium hydroxide, ammonium acetate, ammonium bicarbonate and ammonium phosphate.

6. The method of claim 4 where the alkali metal bases are selected from the group consisting of sodium nitrite, potassium nitrite, sodium cyanide, sodium acetate, sodium hypochlorite, potassium hypochlorite, magnesium carbonate, magnesium oxide and zinc oxide.

7. The method of claim 4 wherein the catalyst is copper tetrammino sulfate.

8. The method of claim 4 wherein the catalyst is a cobalt nitrate tetrammino carbonate complex.

9. The method of claim 4 wherein the catalyst is copper sulfate and the solvent is hexamethylphosphoramide.

10. The method of claim 4 wherein the catalyst is present in an amount of 0.05 to 0.1 g to 1.2 g 2,2',4,4',6,6'-hexanitrobibenzyl reactant.

* * * * *